United States Patent
McCrane

[11] Patent Number: 5,819,313
[45] Date of Patent: Oct. 13, 1998

[54] WRIST GUARD

[76] Inventor: David P. McCrane, 1755 Industrial Way, #1, Napa, Calif. 94558

[21] Appl. No.: 597,504

[22] Filed: Feb. 2, 1996

[51] Int. Cl.⁶ .................................................. A41D 13/08
[52] U.S. Cl. .............................. 2/16; 2/20; 2/162; 473/62
[58] Field of Search ................................ 2/16, 20, 161.1, 2/159, 160, 162; 473/62; 602/21

[56] References Cited

U.S. PATENT DOCUMENTS

| | | |
|---|---|---|
| D. 274,386 | 6/1984 | Tanaka . |
| D. 294,983 | 3/1988 | Purin . |
| 608,303 | 8/1898 | Rife ................................................. 2/20 |
| 3,533,407 | 10/1970 | Smith . |
| 3,598,408 | 8/1971 | Klose . |
| 3,728,738 | 4/1973 | Andolino . |
| 3,770,270 | 11/1973 | Ingold ...................................... 2/161.1 |
| 4,190,906 | 3/1980 | Patton . |
| 4,198,709 | 4/1980 | Clayton . |
| 4,228,548 | 10/1980 | Cohen ...................................... 2/161.1 |
| 4,374,439 | 2/1983 | Norman . |
| 4,658,441 | 4/1987 | Smith ...................................... 2/161.1 |
| 4,850,341 | 7/1989 | Fabry . |
| 4,862,877 | 9/1989 | Barber . |
| 4,883,073 | 11/1989 | Aziz . |
| 4,958,384 | 9/1990 | McCrane . |
| 5,133,233 | 7/1992 | Erwin ......................................... 2/160 |
| 5,267,943 | 12/1993 | Dancyger . |
| 5,313,667 | 5/1994 | Levine ....................................... 2/162 |
| 5,339,465 | 8/1994 | Kyewski . |
| 5,350,343 | 9/1994 | DaSilva . |
| 5,404,591 | 4/1995 | Brinnand . |
| 5,417,645 | 5/1995 | Lemmen . |
| 5,435,007 | 7/1995 | Kalvestran . |
| 5,445,566 | 8/1995 | Hayes ...................................... 2/161.1 |
| 5,538,501 | 7/1996 | Caswell ....................................... 2/16 |
| 5,566,389 | 10/1996 | Li .............................................. 2/162 |

*Primary Examiner*—Bibhu Mohanty
*Attorney, Agent, or Firm*—Flehr Hohbach Test Albritton & Herbert LLP

[57] ABSTRACT

A wrist guard to protect against injury to a person's hand or wrist when engaging in active sports. The guard comprises a body having a palm portion which carries a palm splint, a wrist portion having a cuff edge which fits about the user's wrist, and a flap portion which carries an elongated strap. The body carries a back splint secured to its backside as well as a thumbhole which fits about the user's thumb. Fasteners are provided for releasably fastening both the flap portion and the strap in a closed position about the user's wrist. The outer edge of the flap portion is configured so that when in a closed position it is substantially out of restraining relationship with the little finger side of the user's hand to enable the hand to laterally flex.

12 Claims, 4 Drawing Sheets

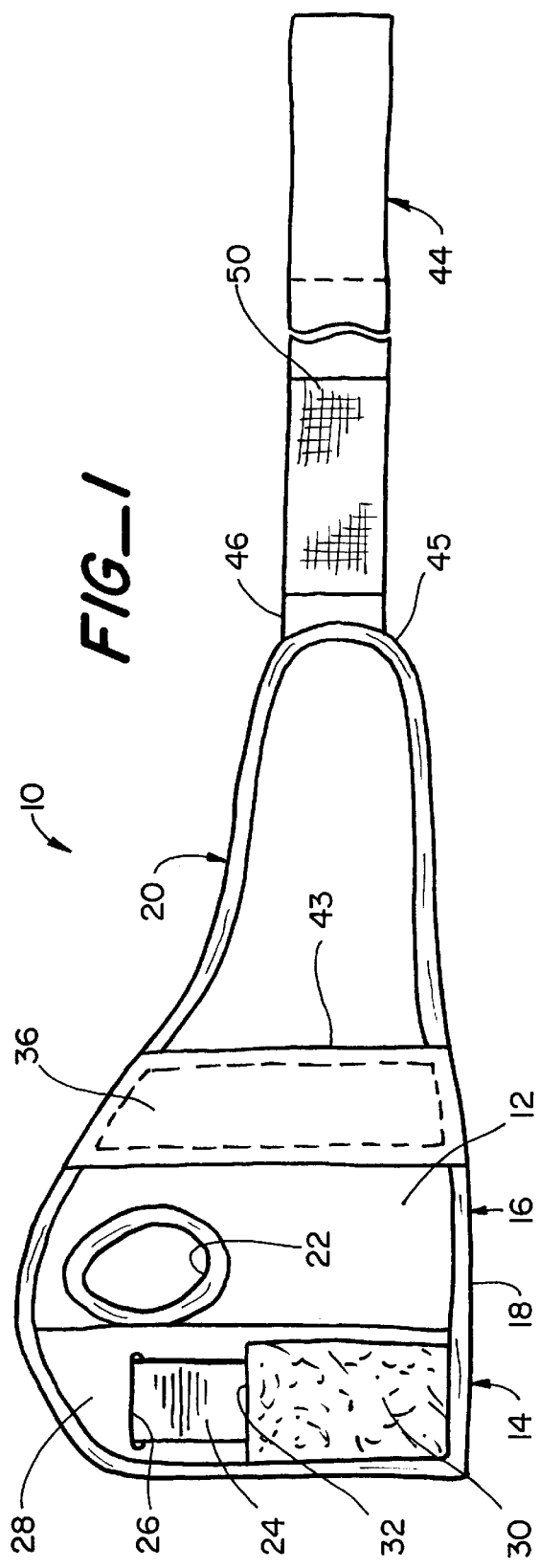
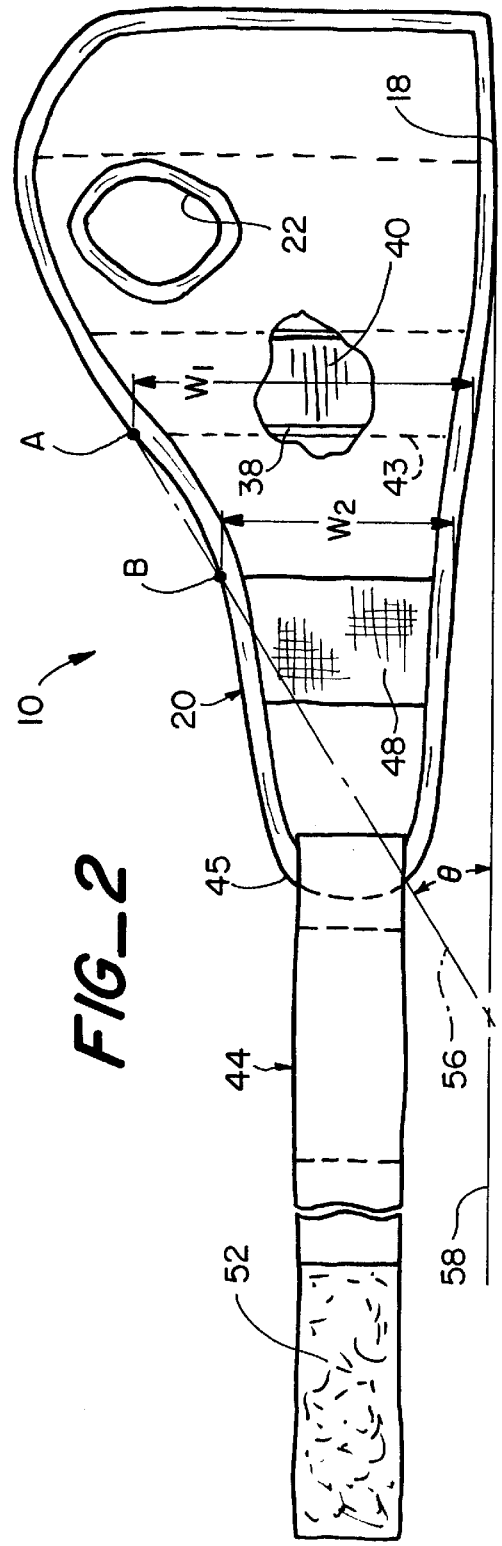

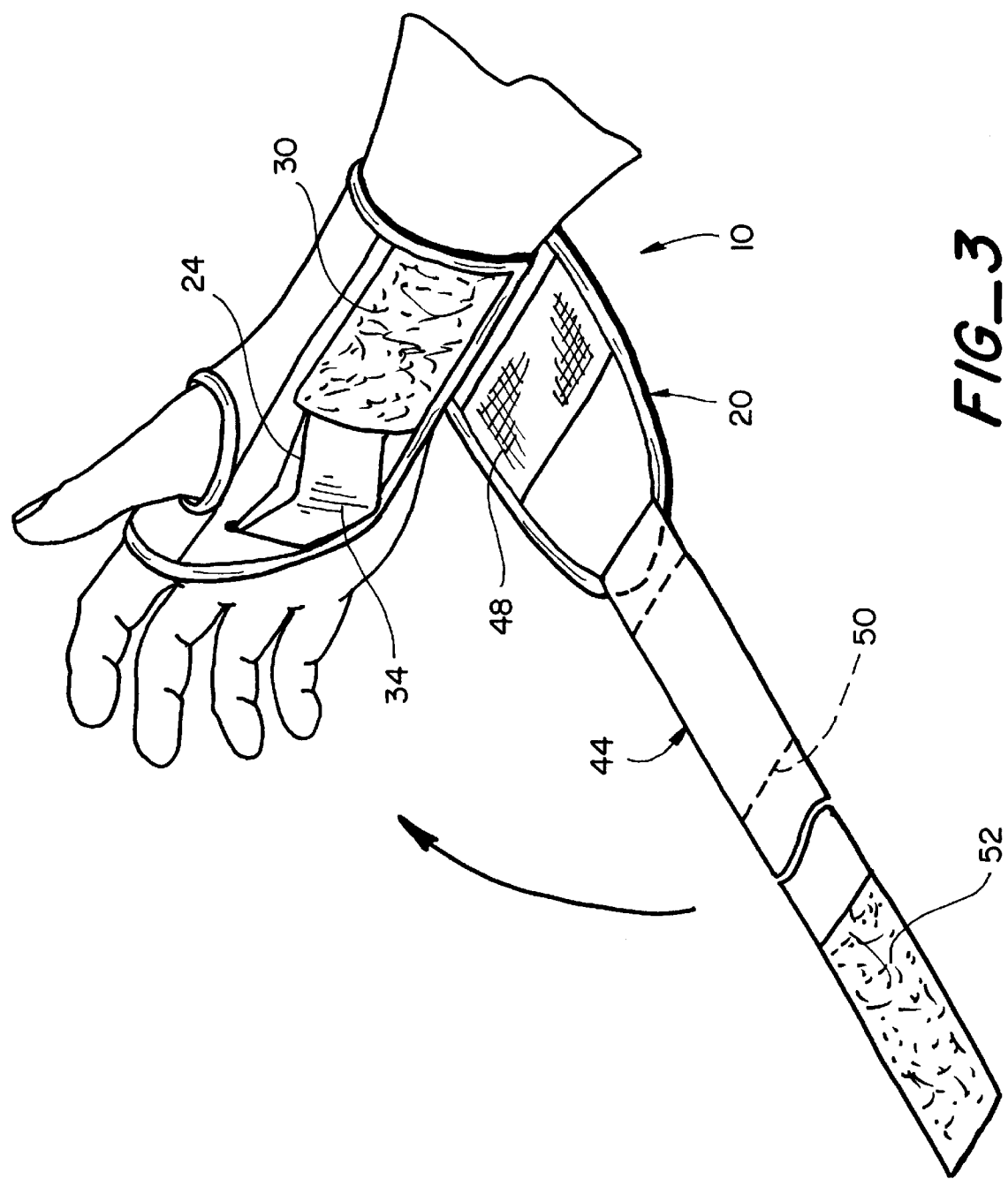
FIG_3

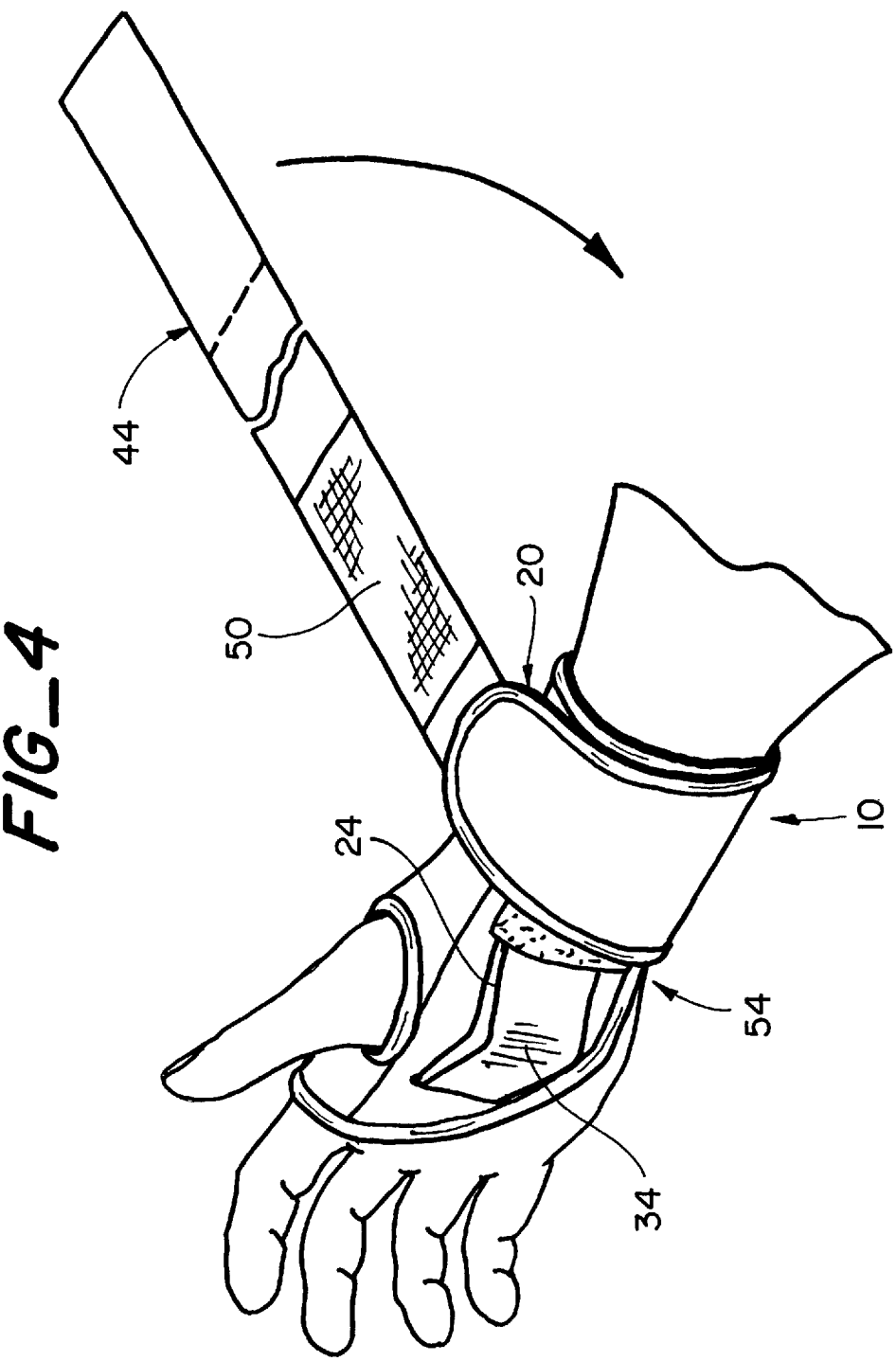

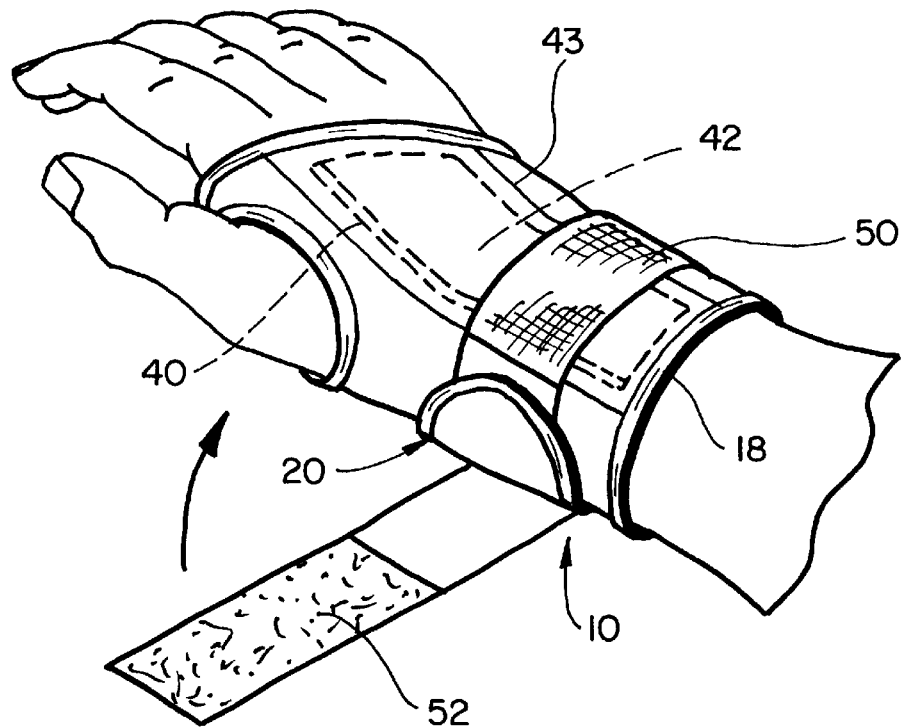
FIG_5
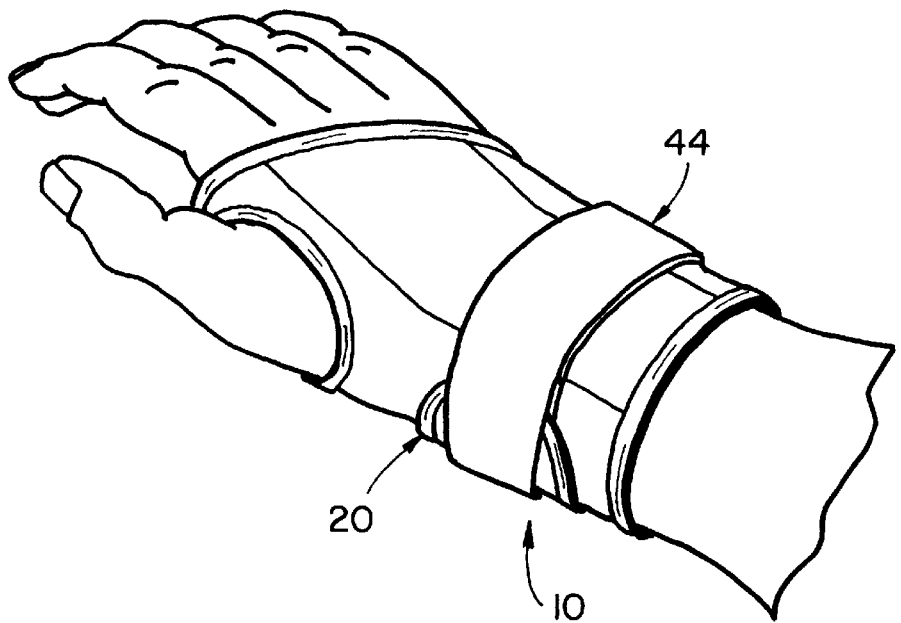
FIG_6

WRIST GUARD

BACKGROUND OF THE INVENTION

1. Field of the Invention

This invention relates to wrist guards for use in protecting the hand and wrist of a person engaged in active sports such as in-line skating, skateboarding, roller skating, snowboarding and the like.

2. Description of the Related Art

Wrist guards are known in the art for protecting the hands and wrist from injury in active sports. Such injuries are common when the user falls in a manner that the hand or wrist strikes the pavement, ground or other hard surfaces.

The prior art wrist guards generally include a flexible layer which carries a palm splint, also known as a skid plate that is typically made of a hard plastic material, together with a back splint. The purposes of the palm splint are to stiffen the wrist and to dissipate part of the energy during a fall by enabling the plate to hit the surface and slide or skid over the surface. The back splint serves to stiffen the wrist and limit hyper-extension of the wrist during a fall.

Thumbholes are provided in the prior art wrist guards for fitting over the user's thumb such that the palm splint is positioned along the user's palm and the back splint is positioned over the back of the hand and wrist. In a typical prior art configuration, the guard is secured about the hand and wrist by means of a pair of short straps which are fastened by means which typically comprise complementary hook and loop fasteners of the type sold under the trademark Velcro. A center strap, positioned between the first two straps, wraps around the wrist in an opposite direction as an additional fastener means.

Despite the availability of the prior art wrist guards, wrist injuries still remain the number one source of injuries to participants in skateboarding and in-line skating because of a number of limitations. Among these limitations are the restrictions in freedom of movement of a user's hand due to the design of the prior art guards. The users desire a greater lateral movement of the hand, such as in street skating for grabbing hand rails or in performing what are called "hand plants" when skating competitively such as in ramp skating or pipe skating. As a result, in the case of existing wrist guards, many participants are deterred from wearing them.

In prior art wrist guards, the palm and back splints make the user's hand so stiff that the guards tend to move the point load, upon impact of the hand with the ground or other surfaces, from the wrist up to the lower arm. As a result, the person's arm then tends to fracture higher up the arm so that, even though the wrist is protected, serious injury still occurs.

Another limitation in prior art wrist guards is that their designs makes them difficult to tighten the straps sufficient to make a firm enough hold to adequately protect against wrist hyper-extension. A further limitation is that the guards are relatively difficult and cumbersome for the user to put on his or her wrist. This results from the fact that the user must wrap and secure each of three separate straps using only one free hand. The standard way to mount the conventional guards is for the user to first wrap and secure the center strap and then secure the two side straps. Because of this relatively complicated procedure, the guard oftentimes is not properly cinched about the wrist.

The need has therefore been recognized for a wrist guard which obviates the foregoing and other limitations and disadvantages of prior art guards. Despite the various wrist guards in the prior art, there has heretofore not been provided a suitable and attractive solution to these problems.

OBJECTS AND SUMMARY OF THE INVENTION

A principal object of the present invention is to provide a wrist guard that obviates the limitations and disadvantages of prior art wrist guards for use in active sports such as in-line skating, skateboarding, roller skating, snowboarding and the like.

A more specific object is to provide a wrist guard of the type described which provides adequate protection against hand and wrist injuries while enabling a greater range of lateral movement of the hand.

Another object is to provide a wrist guard of the type described which enables the user's wrist to be held firmer for providing greater protection against wrist hyper-extension.

Another object is to provide a wrist guard of the type described which prevents hyper-extension of the wrist while also obviating the problem of movement of the point load, upon impact against the hand, from the wrist up to the lower arm.

Another object is to provide a wrist guard of the type described which is easier and less cumbersome for the user to put on and wear.

The invention in summary provides a wrist guard comprising a flexible planar body having a palm portion which carries a palm splint. The body includes a wrist portion having a cuff edge which extends at least partially about the user's wrist, and a flap portion which at least partially wraps about the wrist. The flap portion has an outer edge which, when the flap portion is wrapped about the wrist, is in a position which is substantially out of interfering relationship with the little finger side of the user's hand to enable lateral flexure of the hand. An elongated strap carried by the flap wraps around the wrist.

The foregoing and additional objects and features of the invention will appear from the following specification in which the several embodiments have been set forth in detail in conjunction with the accompanying drawings.

BRIEF DESCRIPTION OF THE DRAWINGS

FIG. 1 is a backside view of a wrist guard in accordance with a preferred embodiment of the invention.

FIG. 2 is a front side view of the wrist guard of FIG. 1.

FIG. 3 is a perspective view illustrating the wrist guard of FIG. 1 in a first step for wrapping it around a user's hand and wrist.

FIG. 4 is a perspective view similar to FIG. 3 showing a further step in wrapping the guard around the user's hand and wrist.

FIG. 5 is a perspective view similar to FIG. 4 showing a still further step in wrapping the guard about the hand and wrist.

FIG. 6 is a perspective view similar to FIG. 5 showing the guard completely wrapped around the hand and wrist.

DESCRIPTION OF THE PREFERRED EMBODIMENTS

In the drawings, the wrist guard embodying a preferred embodiment of the invention is illustrated generally at 10. The guard 10 is comprised of a planar body 12 formed of a suitable material providing flexibility as well as strength. Materials suitable for this purpose comprise nylon, polyester, cotton fabric or leather, or a combination of the foregoing.

Body 12 is shaped to form a palm portion 14 which is adapted to fit against the palm of the user's hand, a wrist portion 16 having a cuff edge 18 which extends at least partially around the user's wrist, and a flap portion 20. FIG. 1 illustrates the backside of the body while FIG. 2 illustrates the front side. A thumbhole 22 is formed in the wrist portion for fitting over the user's thumb. The guard 10 shown in the drawings is adapted for fitting onto the right hand and wrist, and a mirror-image mating guard, not shown, would be provided for the left hand and wrist.

A palm splint 24, also known as a skid plate, is secured to the backside of the palm portion. The palm splint preferably is formed of a durable hard material having a low co-efficient of friction. Semi-rigid plastics such as polyethylene, fiberglass or nylon are suitable for this purpose. The splint is formed in an elongated rectangular shape. Its upper end is fitted within a pocket formed by a slot 26 in a strip 28, which can be of vinyl material, that is sewn onto the backside of the palm portion. A pad 30 is sewn onto the lower part of strip 28, and a slot 32 in the strip above the pad is open to form a pocket into which the lower end of the palm splint is fitted. The outer surface of the pad is comprised of complementary hook or loop material such as that sold under the trademark VELCRO. The portion of the palm splint which is exposed between the two pockets is formed into an outwardly convex arched shape 34, as best shown in FIGS. 3 and 4. The apex of this arched shape provides a low friction skid surface for contacting and sliding along the pavement, ground or the hard surface which is struck by the user's hand, such as during a fall. When the palm splint hits the surface and slides in this manner, it dissipates part of the energy of the fall to reduce the impact and lessen the chances of injury.

An elongated pad 36 is sewn onto the backside of the body at a position between the thumbhole and flap portion 20. The space between the pad and backside of the wrist portion forms a pocket 38 into which a back splint 40 is fitted (FIG. 2). The back splint is formed of a suitable hard, rigid material such as plastic, fiberglass or metal. The midspan 42 of the splint between its upper and lower ends is bent into an outwardly concave shape, as shown in FIG. 5. This shape permits the user's wrist to flex upwardly relative to the wrist through a small angle, such as on the order of 20°. The splint resists flexure of the hand beyond that angle to prevent hyper-extension when the hand receives severe impact forces, such as during a fall.

Flap portion 20 in the preferred embodiment has a length which extends from its proximal end at line 43 to the distal end 45. When the guard is fitted on the hand, proximal end line 43 extends along the back of the hand as shown in FIG. 5. The proximal end has a width $W_1$ (FIG. 2) along line 43 which is sufficiently wide to evenly distribute the flap's tension forces across the width of wrist portion 16 to firmly hold the body in place.

An elongated strap 44 is mounted at is proximal end 46 to the outer end of flap portion 20. The strap is formed of a suitable strong and flexible material, such as nylon. Preferably the strap and flaps are inelastic, although one or more sections of either the strap or flap could be made of an elastic material so that they can be stretched to a limited extent. The length of the strap is made sufficient so that the combined flap portion and strap can wrap at least one turn about the user's wrist when the flap portion is in the closed position shown in FIG. 6. In the illustrated embodiment, the combined flap portion and strap are shown as wrapping just over two turns. In an alternate embodiment, strap 44 as a separate component could be eliminated and flap portion 20 then made sufficiently elongated to wrap at least one turn around the wrist. In such an embodiment, fasteners such as Velcro pads could be secured to the flap tip and corresponding area of the glove body or flap.

Fastener means is provided for releasably fastening flap portion 20 in its closed position to the backside of the body. The fastener means comprises a pad 48 having complementary hook and loop material such as Velcro sewn onto the front side of the flap portion at the position shown in FIG. 2. This position is located so that, when the flap portion is wrapped to its closed position about the wrist, portions of the pads 30 and 48 are in register to interengage their respective hook and loop materials. FIG. 3 shows the positions of these two pads just prior to interengagement.

Fastener means is also provided for releasably fastening the strap 44 about the user's wrist. This fastener means comprises a first pad 50 of complementary hook or loop Velcro material secured as by sewing to the backside of the strap at its proximal end together with a second pad 52, also of complementary hook or loop material, secured as by sewing to the front side of the strap at its distal end. The distance between the two pads is established so that, when the strap is wrapped around the wrist to the fully closed position of FIG. 6, portions of the pads are in register to enable their respective hook and loop materials to be releasably interengaged.

It is an important feature of the invention that flap portion 20 is configured so that, when it is wrapped around the user's wrist, it is substantially out of restraining relationship with the little finger side of the user's hand. This creates a V-shaped gap 54 (FIG. 4) in the guard which enables the hand to laterally flex on the little finger side with respect to the wrist. This in turn enables a greater range of lateral movement of the hand to facilitate, for example, the user grabbing a hand rail in street skating or in doing "hand plants" in competitive ramp skating or pipe skating. For this purpose, the outer edge portion of the flap portion tapers down from point "A" (FIG. 2) at line 43 adjacent the back splint to point "B" adjacent pad 48 along a path 56 which converges at a predetermined angle θ with a line 58 that projects along cuff edge 18. The predetermined angle θ is in the range of 20°–45°, and preferably 30°. With a typical wrist guard having this configuration, the vertical width $W_1$ of the flap portion measured from point A is approximately 4⅞" and the width $W_2$ measured from point B is 3½".

In use, the wrist guard 10 is first fitted on the user's hand by placing the thumb through the thumbhole with the palm portion of the body fitting against the user's palm in the position shown in FIG. 3. Using the opposite hand the strap 44 is then grasped and pulled in an outward direction to draw the flap portion taut. The strap and flap portion are then wound in a clockwise direction, from the viewpoint of the user, while maintaining tension to the position shown in FIG. 4 where pads 30 and 48 interengage and releasably fasten together. The winding motion is continued, while still maintaining tension in the strap, through 270° to the position shown in FIG. 5. The clockwise winding then continues through 180° until Velcro pads 50 and 52 of the strap come together and interengage. This is the fully closed position shown in FIG. 6.

The foregoing wrapping procedure makes it easier and less cumbersome for the user to put the wrist guard on. The user's free hand can more easily wind the flap portion and strap in one continuous motion around the wrist up to the fully closed position. Only one strap needs to be handled to accomplish this, as compared to the multiple straps in many of the prior art wrist guards. Because the user can maintain continuous tension on the strap throughout the procedure, both the flap portion and the strap can be tightly wrapped when the Velcro fasteners are secured. This produces a firmer hold on the wrist and provides greater protection against wrist hyper-extension. Moreover, while maintaining this firm hold about the wrist, the downward tapering or convergence of the outer edge of the flap portion at gap 54 allows for a greater range of lateral movement of the hand. The lateral movement capability, in combination with the palm splint, enables the guard to prevent wrist hyper-extension while also obviating the problem of movement of the point load, upon impact of the hand with the ground or other surface, from the wrist up to the lower arm. The risk of fracture to both the wrist and arm is thereby reduced.

While the foregoing embodiments are at present considered to be preferred, it is understood that numerous variations and modifications may be made by those skilled in the art and it is intended to cover in the appended claims all such variations and modifications as fall within the true spirit and scope of the invention.

What is claimed is:

1. A wrist guard for use in active sports, the wrist guard comprising the combination of:

a body having a front side and a back side, the body being formed of a layer of material which is sufficiently flexible to enable the body to conform about a portion of the user's wrist, the body defining a palm portion which fits against the palm of a user's hand, a wrist portion having a cuff edge which extends at least partially about the user's wrist, and a flap portion which in a closed position extends from one side of the body to at least partially wrap around the user's wrist, the body further defining a thumb area shaped to a least partially encircle the user's thumb;

a palm splint secured to the palm portion, said palm splint having a low friction skid surface which is exposed outwardly from the palm portion for slipping contact with and for absorbing a portion of the force of contact against a surface; and said flap portion having an outer edge which tapers continuously along a path which converges with a line that projects through the cuff edge, said outer edge when the flap portion is wrapped around the user's wrist being in a position creating a gap which is substantially out of restraining relationship with the little finger side of the user's hand to enable the hand to laterally flex on the little finger side with respect to the wrist.

2. A wrist guard as in claim 1 in which said path of the outer edge of the flap portion tapers from a first width adjacent the thumb area to a second width which is less than the first width by an amount which is sufficient to cause said outer edge to be in said position which is substantially out of interfering relationship with the little finger side of the user's hand.

3. A wrist guard as in claim 1 in which said path of the outer edge converges with said line at a predetermined angle which is sufficient to cause said outer edge to be in said position which is substantially out of restraining relationship with the little finger side of the user's hand.

4. A wrist guard as in claim 3 in which said predetermined angle is in the range of from substantially 20° to 45°.

5. A wrist guard as in claim 1 which includes an elongated strap having a proximal end carried by the flap portion and a distal end extending from the flap portion a length which is sufficient to cause the flap portion and strap in combination to wrap at least one turn around the wrist.

6. A wrist guard as in claim 5 which includes fastener means for releasably fastening the strap about the user's wrist.

7. A wrist guard as in claim 6 in which the fastener means comprises a pair of complementary hook and loop pads with one of the pads being mounted on the back side of the strap at its proximal end and the other of the pads being mounted on the front side of the strap at its distal end at a position which registers with at least a portion of said one pad when the strap is wrapped around the user's wrist.

8. A wrist guard as in claim 1 in which the thumb area has an opening positioned adjacent the palm splint for fitting about the user's thumb.

9. A wrist guard as in claim 1 which includes a back splint secured to the back side of the body.

10. A wrist guard as in claim 1 in which said flap portion is substantially inelastic.

11. A wrist guard as in claim 5 in which said strap is substantially inelastic.

12. A wrist guard as in claim 11 in which said flap portion is substantially inelastic.

* * * * *